(12) United States Patent
Blaber et al.

(10) Patent No.: US 7,659,379 B1
(45) Date of Patent: *Feb. 9, 2010

(54) MUTANTS OF HUMAN FIBROBLAST GROWTH FACTOR HAVING INCREASED STABILITY AND/OR MITOGENIC POTENCY

(75) Inventors: Michael Blaber, Tallahassee, FL (US); Vikash Kumar Dubey, West Champaran, Bihar (IN)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/125,174

(22) Filed: May 22, 2008

Related U.S. Application Data (63) Continuation-in-part of application No. 11/983,206, filed on Nov. 7, 2007, and a continuation-in-part of application No. 11/983,215, filed on Nov. 7, 2007, and a continuation-in-part of application No. 11/983,217, filed on Nov. 7, 2007.

(60) Provisional application No. 60/939,909, filed on May 24, 2007.

(51) Int. Cl.
*C07K 14/50* (2006.01)
*C12N 15/18* (2006.01)

(52) U.S. Cl. .................................... 530/399; 536/23.51

(58) Field of Classification Search ...................... None
See application file for complete search history.

(56) References Cited

OTHER PUBLICATIONS

Brych et al. Protein Science, 12: 2704-2718, 2003.*
Brych et al. Journal of Molecular Biology, 344: 769-780, 2004.*

* cited by examiner

*Primary Examiner*—Christine J Saoud
(74) *Attorney, Agent, or Firm*—Allen, Dyer, Doppelt, Milbrath & Gilchrist, P.A.

(57) ABSTRACT

Mutants of human FGF-1 are disclosed having increased stability and mitogenic potency. In the FGF-1 polypeptide, primarily residues 12 and 134 are substituted with cysteine, valine or threonine to render the polypeptide more stable and/or to increase its mitogenicity.

6 Claims, 6 Drawing Sheets

FIG. 6

```
                        SEQUENCE LISTING

<160> NUMBER OF SEQ ID NOS: 1

<210> SEQ ID NO 1
<211> LENGTH: 140
<212> TYPE: PRT
<213> ORGANISM: Homo sapiens
<220> FEATURE:
<221> NAME/KEY: MISC_FEATURE
<223> OTHER INFORMATION: Human FGF-1 wild-type polypeptide

<400> SEQUENCE: 1

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Pro Leu Pro Val Ser Ser Asp
    130                 135                 140
```

MUTANTS OF HUMAN FIBROBLAST GROWTH FACTOR HAVING INCREASED STABILITY AND/OR MITOGENIC POTENCY

RELATED APPLICATION

This application is a continuation in part of Ser. Nos. 11/983,206, 11/983,215 and 11/983,217 all filed on 11 Nov. 2007, and also claims priority from provisional application Ser. No. 60/939,909, filed on 24 May 2007, all of which applications are incorporated herein by reference in their entirety.

FIELD OF THE INVENTION

The present invention relates to the field of protein engineering and, more particularly, to engineered mutant polypeptides of human fibroblast growth factor 1 (FGF-1) having improved thermal stability and/or improved mitogenic activity.

BACKGROUND OF THE INVENTION

The β-trefoil protein human fibroblast growth factor-1 (FGF-1) is made up of a six-stranded anti-parallel β-barrel closed off on one end by three β-hairpins, thus exhibiting a three-fold axis of structural symmetry. The N- and C-termini β-strands hydrogen bond to each other and are postulated from both NMR and X-ray structure data to represent a structurally-weakened region of the β-barrel. Val mutations within the N- and C-termini β-strands are shown to stabilize the structure and to increase van der Waals contacts by filling local cavities present within this region. Mutations that increase van der Waals contacts between both the N- and C-termini β-strands are associated with significant reductions in the unfolding kinetics, and also increase the cooperativity of unfolding. These results indicate that an important step in the unfolding of FGF-1 involves the melting of the N- and C-termini. A series of stabilizing mutations are subsequently combined and result in a doubling of the ΔG of unfolding. These mutations simultaneously introduce a three-fold symmetric constraint upon the primary structure. The results support the hypothesis that a symmetric primary structure within a symmetric superfold is a solution to achieve a foldable polypeptide. The results also suggest that the β-trefoil is capable of substantial thermal stability. When considering the "function/stability trade-off" hypothesis, the β-trefoil architecture therefore appears capable of diverse functional adaptation.

Accordingly, mutants of human fibroblast growth factor 1 (FGF1) are described that have enhanced stability and mitogenic potency. In comparison to wild-type FGF1, polypeptides having mutations at positions 12 and 134 exhibit enhanced properties of stability and/or mitogenic activity. Enhanced stability may preclude the need for added heparin in formulations of FGF1 for therapeutic use. Additionally, the enhanced thermal stability may translate to a longer shelf-life and minimization of aggregation during storage. The enhanced mitogenicity, which is possibly related to enhanced stability, may provide for use of smaller dosages for equivalent efficacy.

SUMMARY OF THE INVENTION

With the foregoing in mind, the present invention advantageously provides a mutant polypeptide of human FGF1, the polypeptide consisting of SEQ ID NO:1 wherein residue 12 is substituted by cysteine. In other embodiments, this mutant further comprises residue 134 substituted by cysteine, valine or threonine.

The invention also provides a mutant polypeptide of human FGF1, the polypeptide consisting of SEQ ID NO:1 wherein residue 12 is substituted by valine. This mutant may also further comprise residue 134 substituted by cysteine, valine or threonine.

A further embodiment of the invention includes a mutant polypeptide of human FGF1, the polypeptide consisting of SEQ ID NO:1 wherein residue 12 is substituted by threonine. This mutant may further comprise residue 134 substituted by cysteine, valine or threonine. In this embodiment, residues 46, 87 or 134 may be substituted by valine.

Moreover, the present invention includes an isolated nucleic acid comprising a sequence that encodes a human FGF-1 polypeptide containing the amino acid sequence of SEQ ID NO:1 wherein residue 12 is substituted by cysteine. This embodiment may further include the FGF-1 polypeptide wherein residue 134 is substituted by cysteine, valine or threonine.

Also included in the invention is an isolated nucleic acid comprising a sequence that encodes a human FGF-1 polypeptide containing the amino acid sequence of SEQ ID NO:1 wherein residue 12 is substituted by valine. In this preferred embodiment, the encoded FGF-1 polypeptide may further comprises residue 134 substituted by cysteine, valine or threonine.

Yet additionally, the invention includes an isolated nucleic acid comprising a sequence that encodes a human FGF-1 polypeptide containing the amino acid sequence of SEQ ID NO:1 wherein residue 12 is substituted by threonine. This embodiment may further comprise wherein the encoded FGF-1 polypeptide further comprises residue 134 substituted by cysteine, valine or threonine.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Figure 1:
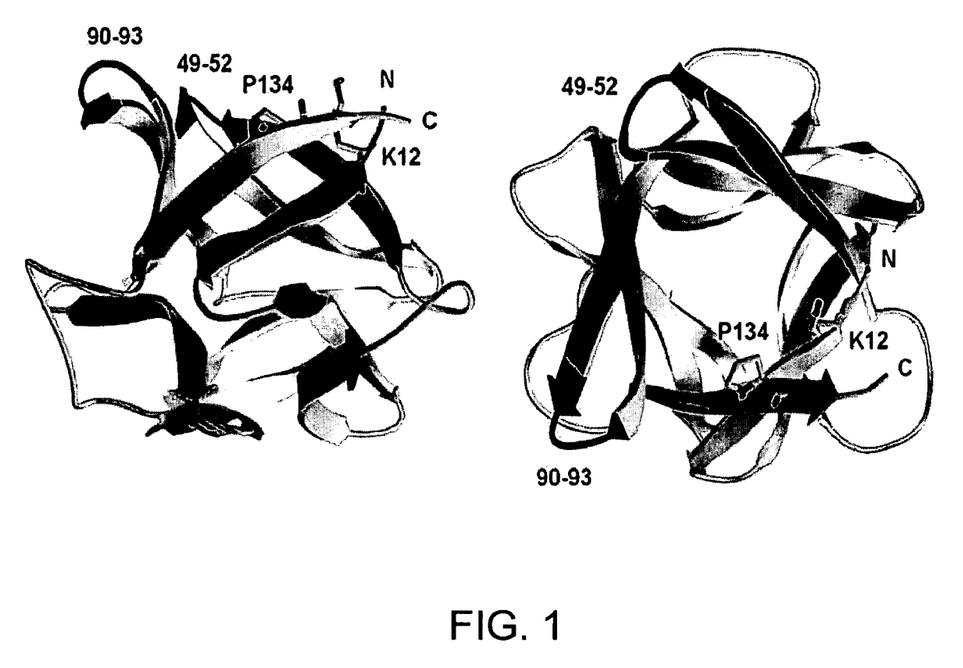
FIG. 1 is a ribbon diagram of FGF-1,[18] showing the location of positions Lys12 and Pro134; the view on the right is looking down the β-barrel axis; also shown are the turn regions (residues 49-52 and 90-93) related to the N- and C-termini by the pseudo-three-fold axis of symmetry inherent in the β-trefoil architecture.
Figure 2:
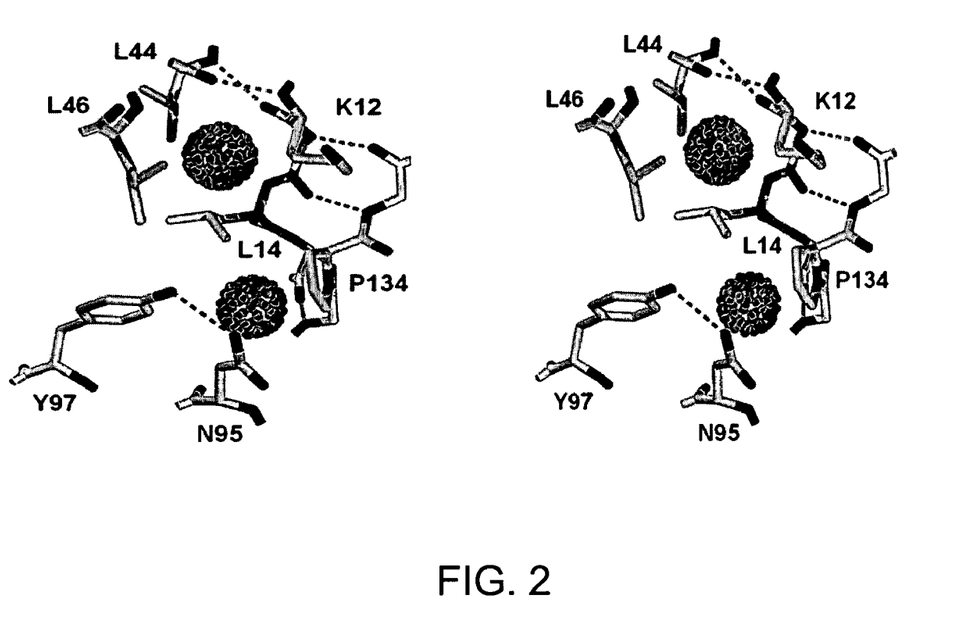
FIG. 2 is a relaxed stereo diagram of the local structure of FGF-1 in the region of positions Lys12 and Pro134 and including the hydrogen-bonding network; also shown are two small solvent excluded cavities, detectable using a 1.2 Å radius probe.

FIGS. 1 through 6 illustrate various aspects of the present disclosure regarding human fibroblast growth factor-1 (FGF-1), which is a potent human mitogen for a variety of cell types, including vascular endothelial cells, and can stimulate such cells to develop neovasculature capable of relieving ischemia. For this reason, FGF-1 is an angiogenic factor with potential applicability in "angiogenic therapy".[1-3] FGF-1 belongs to the β-trefoil superfold.[4,5] This molecular architecture is characterized by a pseudo-3-fold axis of structural symmetry, with the repeating motif being a pair of anti-parallel β-strands, known as the "β-trefoil fold". These repeating structural motifs comprise a total of 12 β-strands that associate to form a six-stranded β-barrel capped at one end by three β-hairpins (forming the "β-trefoil" superfold; FIG. 1). Residue positions 13-17 (using the 140 amino acid form of FGF-1 numbering scheme) of the N-termini (β-strand 1), and 131-135 of the C-termini (β-strand 12), hydrogen bond with each other as a pair of anti-parallel β-strands within the six-stranded β-barrel, closely juxtaposing the two termini. When considering the three-fold symmetry of the overall architecture, the N- and C-termini are structurally related to two β-hairpin turns at positions 49-52 and 90-93 (FIG. 1). Thus, the termini in the native structure represent a break in the mainchain continuity that forms the β-barrel.

An analysis of correlated anisotropic thermal factors in a 1.10 Å atom-resolution x-ray structure of FGF-1, has identified the N- and C-termini β-strands (β-strands 1 and 12, respectively) as demarcating a boundary of domain motion within FGF-1[6]. In the solution NMR structure of FGF-1 the interaction between β-strands 1 and 12 is only consistently defined through residue position 133 in β-strand 12, and the remaining positions 134-135 appear largely disordered[7]. Thus, these data are consistent with the N- and C-termini N-strand interaction representing a region of structural weakness in FGF-1 and therefore potentially contributing to the unfolding process. Of additional interest, quenched-flow hydrogen exchange experiments with FGF-1 have shown that the hydrogen bonds linking the N- and C-termini anti-parallel β strands appear to be the first detectable event in the folding of FGF-1, and may provide a structural framework for subsequent folding events.[8] Thus, in addition to unfolding, the interaction of the N- and C-termini β-strands may be a key contributor to the folding of FGF-1.

In an effort to study the contribution of the N- and C-termini β-strands to the stability and folding of FGF-1, Cys mutations were introduced into each β-strand with the intention of linking them through a disulfide bond. In this case, stability and folding studies under oxidizing and reducing conditions might elucidate the contribution of the N- and C-termini β-sheet formation to these processes. Two potential sites for such pair-wise mutations were identified at positions 12 and 134, and 13 and 135, respectively. These two pair wise Cys mutants were constructed and initial stability studies were performed under oxidizing conditions. The Cys13/Cys135 mutant exhibited a substantial decrease in stability and was not studied further. In contrast, the Cys12/Cys134 mutant exhibited a substantial increase in stability, suggesting that the introduced disulfide bond had stabilized the structure. However, repeating the stability studies under reducing conditions resulted in a further gain in stability. Therefore, the increase in stability for the Cys12/Cys134 mutant was due to the substitution of Lys12 and/or Pro134 by Cys and not to disulfide bond formation. As a consequence of this initial result, additional Thr and Val point mutations were constructed at positions 12 and 134 to probe the nature of the stability increase afforded by the Cys mutations. The results of these studies show that the Cys residue, in each case, is not unique and similar or greater increases in stability can be realized with either Thr or Val mutations.

Isothermal equilibrium denaturation, folding and unfolding kinetics, and x-ray structural studies have been utilized in characterizing the effects of Cys, Thr and Val mutations at positions 12 and 134 in FGF-1. The results show that mutations at both positions 12 and 134 contribute to increased stability, with position 12 mutations primarily increasing the rate of folding, and position 134 mutations primarily decreasing the rate of unfolding. The combined position 12 and 134 Val mutation also exhibits a 30-fold increase in mitogenic potency and may find useful application as a "second generation" form of FGF-1 in angiogenic therapy.

Val mutations at the symmetry-related positions of residues 12 and 134 were also studied and in one case (position 95) provide a substantial additional increase in stability. A combined mutation, involving Val mutations at five positions, and introducing a three-fold symmetric constraint at two positions within the FGF-1 structure, results in an increase in stability that doubles the original value of the ΔG of unfolding. This combined mutation is, however, functionally inactive. The results provide additional support to our hypothesis[9] that a symmetric primary structure within a symmetric superfold is a solution to, and not a constraint upon, the protein folding problem. Furthermore, the results also support the "function/stability trade-off" hypothesis[10-14], and lead us to propose that one property of the β-trefoil superfold (and presumably all the protein superfolds) is the capacity for profound thermal stability, permitting a wide range of adaptive radiation in function.

Materials and Methods

Mutagenesis and Expression

Mutant construction and expression followed previously described procedures.[15-17] Briefly, all studies utilized a synthetic gene for the 140 amino acid form of human FGF-1[18-21] with the addition of an amino-terminal six residue "His-tag" to facilitate purification.[17] In the present study a Cys117⇒Val mutant form of FGF-1 was chosen as the reference protein for the current set of mutations, and is referred to as WT* in this report. The Cys117⇒Val mutation has minimal effects upon stability, folding or function of FGF-1 17 but eliminates a surface exposed cysteine residue that can form an intermolecular disulfide bond. The QuikChange™ site directed mutagenesis protocol (Stratagene, La Jolla, Calif.) was used to introduce individual or combination mutations using mutagenic oligonucleotides of 25 to 31 bases in length (Biomolecular Analysis Synthesis and Sequencing Laboratory, Florida State University). All FGF-1 mutants were expressed using the pET21a(+) plasmid/BL21 (DE3) *Escherichia coli* host expression system (Invitrogen Corp., Carlsbad Calif.). Mutant proteins were purified as previously described[17] using nickel-nitrilotriacetic acid (Ni—NTA) chromatography followed by affinity purification using heparin Sepharose™ chromatography (G.E. Healthcare, Piscataway N.J.). Sites for Cys mutations leading to potential disulfide bond formation were identified using the Disulfide by Design program[22] and the x-ray coordinates of wild-type FGF-1.[18]

Isothermal Equilibrium Denaturation

Isothermal equilibrium denaturation by guanidine hydrochloride (GuHCl) was quantified using fluorescence as the spectroscopic probe. FGF-1 contains a single buried tryptophan residue (Trp107) that exhibits greater fluorescence quenching in the native versus denatured state.[15, 18] The differential fluorescence between the native and denatured state has been used to quantify the unfolding of FGF-1, in excellent agreement with unfolding as monitored by CD spectroscopy.[15, 23] Fluorescence data were collected on a Varian Eclipse fluorescence spectrophotometer equipped with a Peltier controlled temperature regulator at 298K and using a 1 cm path-length cuvette. Protein samples (5 μM) were equilibrated overnight in 20 mM ADA, 100 mM NaCl, 2 mM DTT pH 6.6 ("ADA buffer") at 298K in 0.1M increments of GuHCl. Triplicate scans were collected and averaged, and buffer traces were collected and subsequently subtracted from the protein scans. All scans were integrated to quantify the total fluorescence as a function of denaturant concentration. The general purpose non-linear least squares fitting program DataFit (Oakdale Engineering, Oakdale, Pa.) was used to fit the change in fluorescence versus GuHCl concentration data to a six parameter two-state model[24]:

$$F = \frac{F_{0N} + S_N[D] + (F_{0D} + (S_D[D]))e - (\Delta G_0 + m[D])/RT}{1 + e - (\Delta G_0 + m[D])/RT} \quad (1)$$

where [D] is the denaturant concentration, $F_{0N}$ and $F_{0D}$ are the 0M denaturant molar ellipticity intercepts for the native and denatured state baselines, respectively, and $S_N$ and $S_D$ are the slopes of the native and denatured state baselines, respectively. $\Delta G_0$ and m describe the linear function of the unfolding free energy versus denaturant concentration. The effect of a given mutation upon the stability of the protein ($\Delta\Delta G$) was calculated by taking the difference between the $C_m$ values for WT* and mutant proteins and multiplying by the average of the m values, as described by Pace and Scholtz[25]:

$$\Delta\Delta G = (C_{m\ WT^*} - C_{m\ mutant})(m_{WT^*} + m_{mutant})/2 \quad (2)$$

Folding Kinetics Measurements

Initial studies using manual mixing indicated that the relaxation times for folding were more appropriate for stopped-flow data collection. Denatured protein samples were prepared by overnight dialysis against ADA buffer containing either 2.5 M or 3.0 M GuHCl (depending upon the overall stability of the mutant). All folding kinetic data were collected using a KinTek SF2000 stopped-flow system (KinTek Corp., Austin Tex.). Folding was initiated by a 1:10 dilution of 40 μM denatured protein into ADA buffer with denaturant concentrations varying in increments of 0.05 M or 0.1 M, to the midpoint of denaturation as determined by the above described isothermal equilibrium denaturation measurements. The data collection strategy was designed to span approximately five half-lives, or >97% of the expected fluorescence signal change between the fully denatured and native states.

Unfolding Kinetics Measurements

Unfolding kinetics measurements were performed using a manual mixing technique. Protein samples (~30 μM) were dialyzed against ADA buffer overnight at 298K. Unfolding was initiated by a 1:10 dilution into ADA buffer with a final GuHCl concentration of 1.5 to 5.5M in 0.5M increments. All unfolding data were collected using a Varian Eclipse fluorescence spectrophotometer equipped with a Peltier controlled temperature unit at 298K. Data collection times for each protein were designed so as to quantify the fluorescence signal over 3-4 half-lives, or >93% of the total expected amplitude.

Folding and Unfolding Kinetics Analysis

The folding and unfolding characteristics of FGF-1 have previously been described in detail.[26] Briefly, the unfolding kinetic data exhibits an excellent fit to single exponential decay at all denaturant concentrations. The folding kinetic data also exhibit an excellent fit to a single exponential model, but only for denaturant concentrations above approximately 0.6M GuHCl. Below this concentration, the folding kinetic data exhibit bi-exponential properties; with the slow phase being generally independent of denaturant concentration. The fast phase of this biexponential folding regime lies on the extrapolated region of the single-exponential folding data. Thus, the folding constant is derived from a fit to the monoexponential region and the fast phase of the bi-exponential region. The ΔG values derived from the folding and unfolding kinetic data are in excellent agreement with the values obtained from isothermal equilibrium denaturation data, as well as differential scanning calorimetry.[26]

Both folding and unfolding kinetic data were collected in triplicate at each GuHCl concentration; data from at least three separate experiments were averaged in each case. The kinetic rates and amplitudes versus denaturant concentration were calculated from the time dependent change in tryptophan fluorescence using a single exponential model:

$$I(t) = A\exp(-kt) + C \quad (3)$$

Where I(t) is the intensity of fluorescent signal at time t, A is the corresponding amplitude, k is the observed rate constant for the reaction and C is the asymptote of the fluorescence signal. Folding and unfolding rate constant data were fit to a global function describing the contribution of both rate constants to the observed kinetics as a function of denaturant ("Chevron" plot) as described by Fersht[27]:

$$\ln(k_{obs})=\ln(k_{f0}\exp(mf[D])+\ln(k_{f0}\exp(m_u[D])) \quad (4)$$

where $k_{f0}$ and $k_{u0}$ are the folding and unfolding rate constants, respectively, extrapolated to 0M denaturant, mf and $m_u$ are the slopes of the linear functions relating $\ln(k_f$ and $\ln(k_u)$, respectively, to denaturant concentration, and [D] is the denaturant concentration.

Crystallization of FGF-1 Mutants, X-Ray Data Collection, Refinement and Cavity Calculations Purified protein for crystallization trials was dialyzed against 50 mM sodium phosphate, 100 mM NaCl, 10 mM ammonium sulfate, 2 mM DTT pH 7.5 ("crystallization buffer") and concentrated to 10-16 mg/ml. Crystals were grown at room temperature using the hanging-drop vapor diffusion method with 7 μl drop size and 1 ml of reservoir solution. Diffraction quality crystals grew from reservoirs containing 3.2-4.3 M sodium formate and 0.25-0.5 M ammonium sulfate, with the exception of the Pro134⇒Cys mutant which grew from 3.6M sodium formate with no added ammonium sulfate.

Diffraction data for all mutants except Pro134⇒Cys, was collected at the Southeast Regional Collaborative Access Team (SER-CAT) 22-BM beam line (λ=1.00 Å) at the Advanced Photon Source, Argonne National Laboratory, using a MarCCD225 detector (Mar USA, Evanston, Ill.). Pro134⇒Cys mutant diffraction data was collected using an in-house Rigaku RU-H2R copper rotating anode (λ=1.54 Å) X-ray generator (Rigaku MSC, The Woodlands, Tex.) coupled to an Osmic Purple confocal mirror system (Osmic, Auburn Hills, Mich.) and a MarCCD165 detector (Mar USA, Evanston, Ill.). In all cases, crystals were mounted and maintained in a stream of gaseous nitrogen at 100 K. Diffraction data were indexed, integrated and scaled using the HKL2000 software[28, 29]. His-tagged wild-type FGF-1 (PDB code: 1JQZ) was used as the search model in molecular replacement using the CNS software suite[30]. Model building and visualization utilized the O molecular graphics program[31]. Structure refinement utilized the CNS software suite, with 5% of the data in the reflection files set aside for $R_{free}$ calculations[32]. Quantification of solvent-excluded cavities with the refined mutant structures was performed using the MSP software package[33].

Mitogenic Assay

The mitogenic activity of certain mutants was evaluated by a cultured fibroblast proliferation assay. NIH 3T3 fibroblasts were initially plated in Dulbecco's modified Eagle's medium (DMEM) (American Type Culture Collection, Manassas Va.) supplemented with 10% (v/v) newborn calf serum (NCS) (Sigma, St Louis Mo.), 100 units of penicillin, 100 mg of streptomycin, 0.25 mg of Fungizone™ and 0.01 mg/ml of gentamicin (Gibco, Carlsbad Calif.) ("serum-rich" medium) in T75 tissue culture flasks (Fisher, Pittsburgh Pa.). The cultures were incubated at 37° C. with 5% CO2 supplementation. At 80% cell confluence, the cells were washed with 5 ml cold 0.14 M NaCl, 5.1 mM KCl, 0.7 mM Na2HPO4, 24.8 mM Trizma base, pH 7.4 (TBS) and subsequently treated with 5 ml of a 0.025% trypsin solution (Invitrogen Corp., Carlsbad Calif.). The trypsinized cells were subsequently seeded in T25 tissue culture flasks at a density of 3.0×104 cells/cm2 (representing 20% confluence). Cell synchronization was initiated by serum starvation in DMEM with 0.5% NCS, 100 units of penicillin, 100 mg of streptomycin, 0.25 mg of Fungizone™ and 0.01 mg/ml of gentamicin ("starvation" medium). Cultures were incubated for 48 hours at 37° C., the medium was then decanted and replaced with fresh medium supplemented with FGF-1 (0-10 μg/ml), and the cultures incubated for an additional 48 hours. After this incubation, the medium was decanted and the cells were washed with 1 ml of cold TBS. 1 ml of 0.025% trypsin was then added to release the cells from the flask surface, and 2 ml of serum-rich medium was added to dilute and inhibit the trypsin. The cells were counted using a hemocytometer (Hausser Scientific Partnership, Horsham Pa.). Experiments were performed in quadruplicate and the cell densities were averaged. The relationship between the cell number and log concentration of added growth factor was fit to a sigmoid function. The midpoint of the fitted sigmoid function represents the concentration of added growth factor necessary to achieve 50% stimulation ($EC_{50}$ value), and is used for quantitative comparison of mitogenicity.

Results

Mutant Protein Purification

All mutants were purified with high yield (~65 mg/L).

Isothermal Equilibrium Denaturation

The thermodynamic parameters for the FGF-1 mutants are listed in Table I. The standard error of ΔG from multiple analyses is approximately 1.0 kJ/mol (0.24 kCal/mol), which is also the typical magnitude of the standard deviation of the fit to the 2-state model (data not shown). Thus, mutational effects upon stability can be reliably measured for values greater than 1 kJ/mol, consistent with previous reports, and the mutational effects upon stability are larger than this standard error in each case.

The substitution of Lys12 by Cys, Thr or Val provides a substantial increase in stability of between −6.9 to −8.1 kJ/mol. The highest midpoint of denaturation is observed for the Val mutant (1.53 M); however, a slight reduction in the ΔG versus denaturant m-value for the Val mutant in comparison to Cys results in a somewhat higher ΔG value for Cys when extrapolated to 0M denaturant (Table I). Overall, therefore, the Cys and Val mutants appear to be approximately equivalent in stability, with Thr slightly less so (but still stabilizing the protein by approximately −7.0 kJ/mol). The substitution of Pro 134 by Cys, Thr or Val also provides a significant increase in stability of between −4.7 to −7.6 kJ/mol. The highest midpoint of denaturation is observed for the Val mutant (1.49 M). In the case of position 134 mutations, the ΔG versus denaturant m-value is not substantially altered (table 1), and extrapolation of ΔG to 0M denaturant similarly identifies the Val mutant as the most stable at this position.

Combining Val mutations at positions 12 and 134 results in a −17.7 kJ/mol increase in stability. The simple sum of the individual point mutations predicts an increase in stability of −15.7 kJ/mol; thus, the effects of the combined mutation appear to be largely additive in nature, with the possibility of cooperative interactions providing a modest −2.0 kJ/mol of additional stability.

Folding and Unfolding Kinetics

The results of the folding and unfolding kinetic analyses are listed in table II. The Cys, Thr, and Val mutations at position 12 stabilize the protein by primarily increasing the folding rate constant (4 to 10-fold) with comparatively less-significant (2-fold or less) reduction in the unfolding rate constant. These alterations in the folding and unfolding rate constants are associated with minimal changes in either the folding or unfolding kinetics "m values".

The results of the Cys, Thr, and Val mutations at position 134 upon the folding and unfolding rate constants are a bit more complex. The Cys mutation achieves its increase in stability primarily through an 8-fold increase in the folding rate constant, and less than 2-fold decrease in the unfolding rate constant. Thus, the stability increase for Cys mutations at positions 12 and 134 are due to similar effects upon folding and unfolding kinetic rate constants (i.e. primarily an increase in folding rate constant). The Thr mutation at position 134 achieves its increase in stability through an equivalent 2-fold increase in folding rate constant and 2-fold decrease in unfolding rate constant. The Val mutation at position 134 achieves its stability increase primarily through a 10-fold decrease in unfolding rate constant, but also through an associated 6-fold increase in folding rate constant. Furthermore, the Val mutation is associated with a 2-fold increase in unfolding kinetics "m value" (which is not observed in either the Cys or Thr mutation; Table II). The double Val mutant at positions 12 and 134 exhibits the 10-fold reduction in unfolding rate constant displayed by the Val mutation at position 134, as well as a 33-fold increase in folding rate constant (an enhancement of the 10-fold increase in folding rate constant exhibited by the Val mutant at position 12). This double mutant retains the 2-fold increase in unfolding kinetics "m value" (in comparison to WT*) displayed by the Val mutation at position 134; there is no substantial change in the folding kinetics "m value" in comparison to WT*.

X-Ray Structures

Diffraction-quality crystals were obtained for the Lys12⇒Cys, Lys12⇒Val, Lys12⇒Thr, Lys12⇒Val/Asn95⇒Val and Pro134⇒Cys mutants (the majority of the position 134 mutations proving to be refractory to crystallization). All structures were refined to acceptable crystallographic residuals and stereochemistry. Crystallographic data collection and refinement statistics for the mutants are listed in Table III. All mutants, except Pro 134⇒Cys, crystallized in the WT* orthorhombic space group ($C222_1$) with two molecules in asymmetric unit. The Pro 134⇒Cys mutant crystallized in the monoclinic $P2_1$ space group with four molecules in the asymmetric unit. These four molecules were successfully positioned using the molecular replacement method and WT* FGF-1 as the search model. The $2F_0-F_c$ difference electron density was unambiguous at the mutation site(s), and the mutant structures could be accurately modeled in each case.

Mitogenic Activity

The mitogenic activity ($EC_{50}$) for representative FGF-1 mutants is summarized in table IV (the WT* Cys117⇒Val reference protein is essentially identical to wild-type FGF-1 in terms of stability, folding and mitogenic activity). The Cys and Val mutations at position 12 are approximately equivalent to each other in terms of mitogenic activity, and both are approximately 15 times more potent than WT* FGF-1. In contrast, while the Cys and Val mutations at position 134 are similarly equivalent to each other in terms of mitogenic potential, they exhibit only a modest increase in mitogenic activity compared to WT* (Table IV). The combination Val mutation at positions 12 and 134 appears to be largely additive, exhibiting an approximately 30-fold increase in mitogenic activity compared to WT*. The Val mutation at position 95 exhibits a substantial ~1000-fold reduction in mitogenic activity.

Differential Scanning Calorimetry

Figure 6:
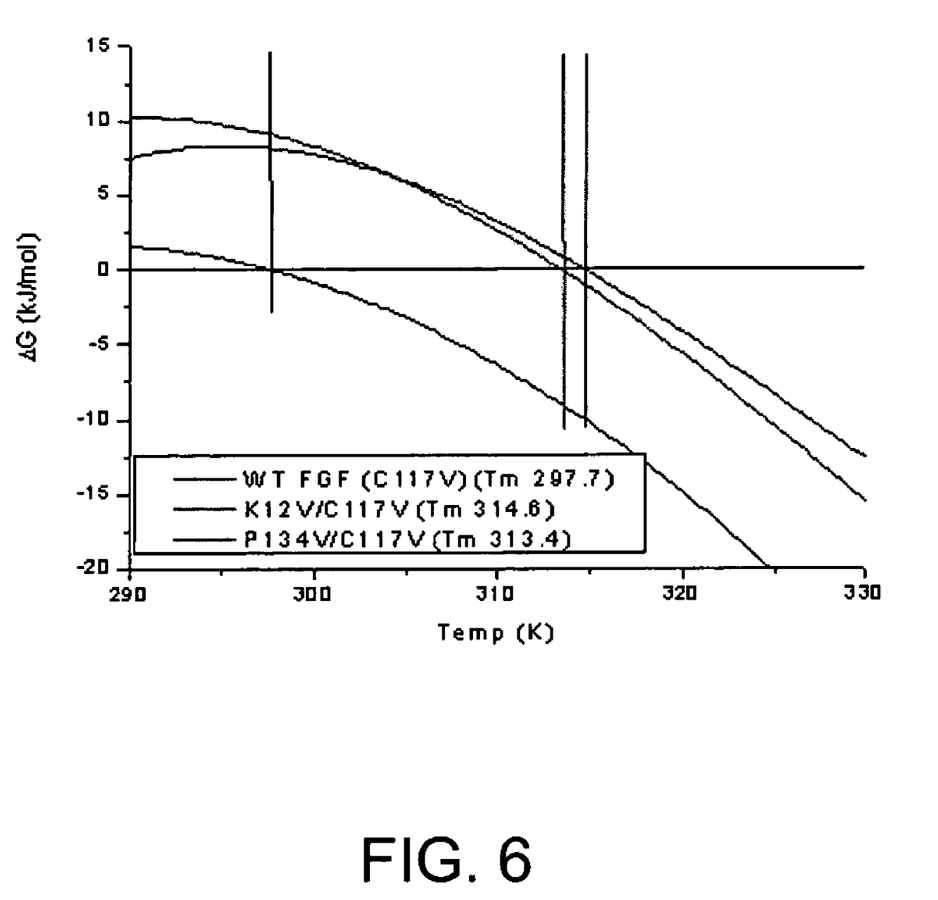
FIG. 6 shows the results of differential scanning calorimetry studies of K12V/C117V FGF-1 (SEQ ID NO:3) and P134V/C117V FGF-1 (SEQ ID NO:9) in comparison to C117V FGF-1 ("wild-type" FGF-1; SEQ ID NO:1).

Differential Scanning Calorimetry studies of K12V/C117V FGF-1 and P134V/C117V FGF-1 were conducted and compared to C117V FGF-1 ("wild-type" FGF-1). We performed thermal denaturation studies of the above mutants using differential scanning calorimetry (DSC). This method permits direct determination of the melting temperature (melting transition midpoint) of a protein. The K12V and P134V point mutations were made in a modified version of wild-type FGF-1 that contains a Cys to Val mutation at position 117. This mutation has no effect upon stability of the protein, however, it eliminates the possibility of disulfide-linked dimers of FGF-1 (which is problematic for DSC analysis). The graph depicted in FIG. 7 shows the derived free energy profile (DG) as a function of temperature for the above mutants and "wild type" FGF-1.

DISCUSSION

Figure 3:
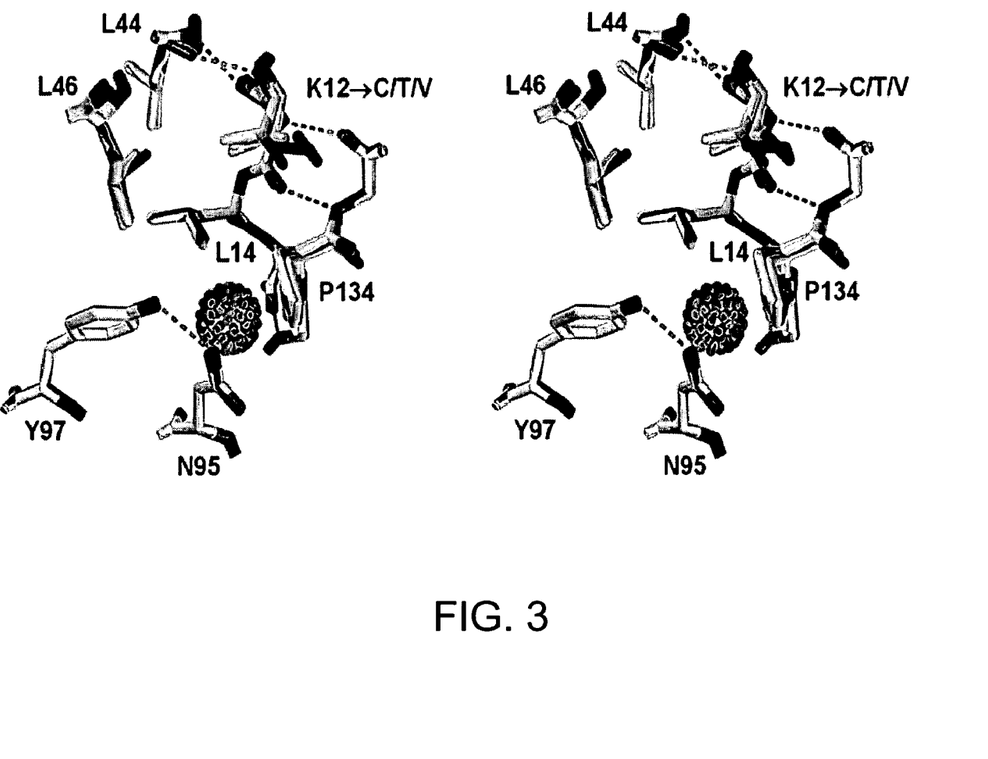
FIG. 3 is a relaxed stereo diagram showing an overlay of the K12→C, K12→T, and K12→V x-ray structures with WT* (dark grey) in the region of the mutation site; the solvent excluded cavity adjacent to position 12 is filled with each mutation.

The x-ray structure of wild-type FGF-1 exhibits two small solvent-excluded cavities, detectable using a 1.2 Å radius probe, in the region of residues 12, 95 and 134 (FIG. 2) and these appear to be key to understanding the effects of the mutations at these positions. One cavity, adjacent to position 12, and bounded by residues 14, 44 and 46, has a volume of 9 Å3; the other cavity, adjacent to position 134, and bounded by residue positions 14, 95 and 97, has a volume of 8 Å$^3$. The WT* Lys residue at position 12 adopts a χ1 angle of −60° (gauche+), which orients the Lys12 side chain away from the adjacent cavity. However, the mutant Cys residue at position 12 adopts a χ1 angle of +60° (gauche-) which positions the side chain Sã towards the nearby cavity (FIG. 3). Both the Thr and Val mutations at position 12 adopt rotamer angles that orient a side chain ã methyl group in the same position as the Cys Sã. Thus, each of these small side chains is oriented so as to fill the adjacent cavity with a non-polar moiety. The Lys12 does not appear capable of adopting a gauche-rotamer (and filling the adjacent cavity) due to resulting steric clashes with adjacent residue Leu46. In filling this adjacent cavity, the Cys, Thr or Val residues are oriented to participate in van der Waals contacts with residues in adjacent β-strand 4, and not β-strand 12. Thus, the observed increase in stability with the position 12 mutants does not appear to be associated with stabilizing interactions between the N- and C-termini β-strands.

Figure 4:
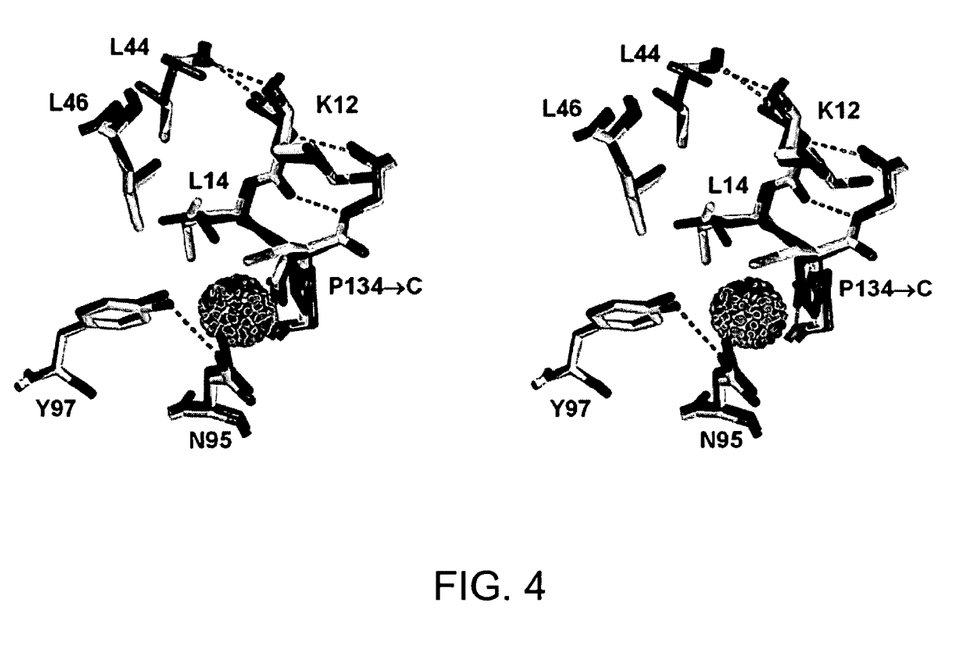
FIG. 4 shows a relaxed stereo diagram showing an overlay of the P134→C x-ray structure with WT* (dark grey) in the region of the mutation site; the solvent excluded cavity adjacent position 12 is no longer detectable due to rotation of the Leu14 side chain.

The X-ray structure of the Cys mutation at position 134 provides an opportunity to understand the structural basis of the increase in stability for mutations at this position. The Cys residue adopts a rotamer angle of −60° (gauche+) (FIG. 4). While generally oriented towards the cavity adjacent to position 134, the mutant Cys Sγ does not appreciably reduce the size of the cavity. However, in response to the introduction of the Cys at position 134, the adjacent residue Leu14 adopts an alternate χ2 angle. This alternative side chain orientation positions one of the Leu Δ methyl groups towards the cavity adjacent to position 12; the result being that this cavity is no longer detectable using a 1.2 Å radius probe. Thus, the mutations at position 134 are capable of reducing the overall cavity space within the local region and increasing van der Waals contacts between β-strand 1 and β-strand 12 (i.e. the N- and C-termini).

Figure 5:
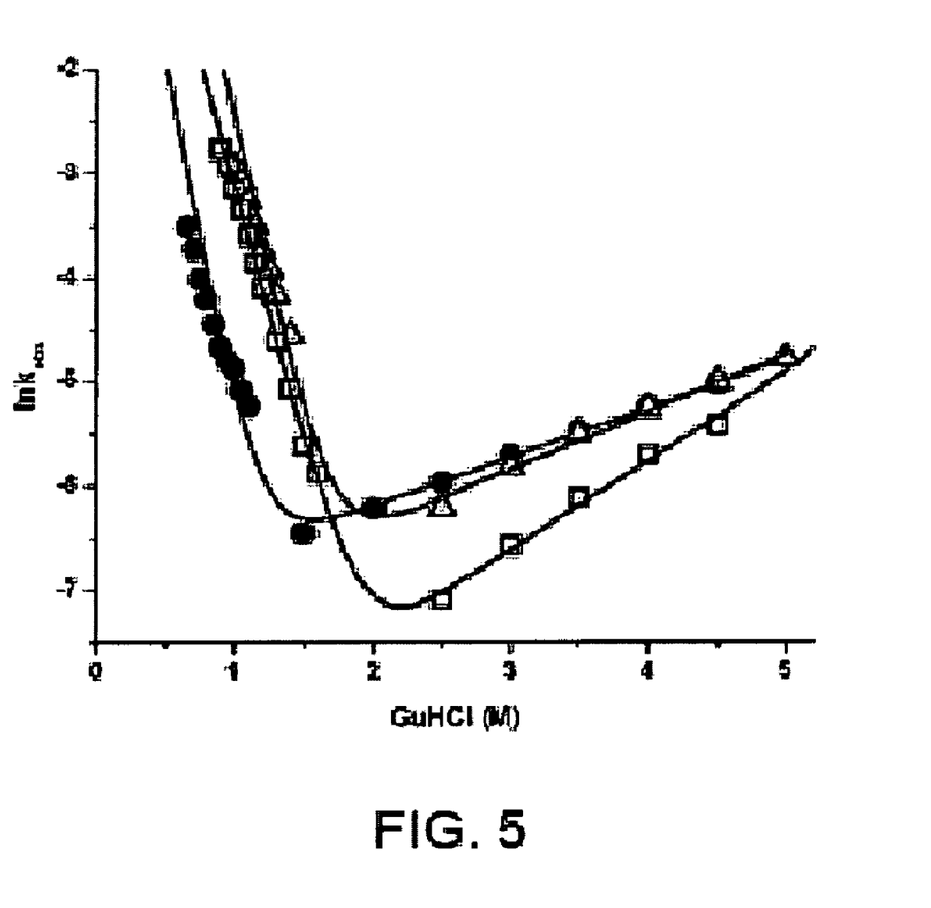
FIG. 5 shows folding and unfolding kinetics "chevron plot" for WT* (●), Lys12→Val (Δ), P134→V(□)

In the x-ray structure of the combined Val mutations at positions 12 and 95, the Val at position 12 behaves the same as the Val 12 point mutation, and fills the adjacent cavity (FIG. 5). In response to the Val mutation at position 95, the Pro side chain at position 134 shifts inward towards the cavity adjacent to this position, with the result that it is no longer detectable using a 1.2 Å radius probe. This structural adjustment results in greater van der Waals interactions between residue position 134 and adjacent residues, including Leu14 on β-strand 1.

Thus, the Val mutation at position 95 also has the result of improving the van der Waals interaction between β-strands 1 and 12 (i.e. the N- and C-termini).

Mutations at position 134, but not position 12, are unique in increasing the unfolding kinetics "m value" (i.e. cooperativity of unfolding; FIG. 6) as well as decreasing the overall unfolding rate constant (table II). An interpretation for an increase in the unfolding kinetics "m value" is that the mutation has introduced stabilizing interactions in the native structure, but not in the folding transition state, as would be expected if additional hydrophobic contacts had been formed in the native structure 34. However, the position 12 mutations have similarly introduced additional hydrophobic contacts in the native state, but have not affected the unfolding kinetics "m value" nor significantly decreased the rate of unfolding. Thus, the distinction is that the mutations that have stabilized interactions between β-strands 1 and 12 are responsible for the decreased unfolding rate constant and increased cooperativity of unfolding. Therefore, it is concluded that early events in the unfolding of FGF-1 likely involve melting of the interaction between β-strands 1 and 12. This interpretation is consistent with the previously described domain motion boundary in FGF-1 involving these β-strands 6, and the solution NMR data indicating partial melting of the interface of β-strand 1 and 12 in FGF-1 at 298K 7. Stabilizing adjacent N- and C-termini β-strand interactions may prove to be a generally-useful approach to engineering increased thermal stability in β-barrel structures, and appears capable of providing a substantial increase to the stability of the protein.

The Val mutations at positions 12 and 134 are approximately equivalent in their favorable contribution to the stability of the protein (~−8.0 kJ/mol). FGF-1 exhibits relatively low thermal stability[15, 35], and mutations that stabilize the structure can increase the effective mitogenic potency, presumably due to longer functional half-life[9]. Both of the Val mutations at positions 12 and 134 appear more functionally active than WT*, although the position 12 mutation has a much more dramatic increases in mitogenicity (table IV). The Lys 12 side chain does not directly interact with FGFR (PDB accession 1 E0O), neither does Pro134. Thus, the basis for the difference in mitogenic activity between the 12 and 134 Val mutants (given their near-identical stability increase) is not fully understood. Nonetheless, the combined Lys12⇒Val/Pro134⇒Val mutant exhibits the greatest mitogenic activity, approximately 30 times more potent than WT*, and is −17.7 kJ/mol more stable than WT*. Such mutant forms of FGF-1 may find application as "second generation" forms of FGF-1 in angiogenic therapy for the treatment of ischemia 3, 36.

The results shown in FIG. 6 indicate that the K12V mutation increases the melting temperature by 16.9° C. and the P13V mutation increases the melting temperature by 15.7° C. This is similar to the increase in stability afforded by the addition of heparin (see Copeland (1)); thus, these mutations may obviate the need to add heparin in the formulation of FGF-1 (saving considerable cost and avoiding concerns of infectious agents, since heparin is derived from pig tissue).[35]

The Cys, Val and Thr mutations at position 12 exhibit closely-related effects as regards their substantial increase in stability. Similarly, the Cys, Val and Thr mutations at position 134 also exhibit closely-related substantial increases in stability. These similar mutagenic effects observed for the set of Cys, Val and Thr amino acids reflect their related stereochemical properties. Of the 20 common amino acids, the set of Cys, Val, and Thr amino acids comprise a unique set: i.e. they are the only amino acids that contain at least a side chain gamma constituent, but no constituent beyond the gamma position (i.e. no delta, epsilon, etc. constituent). The X-ray structure analyses of the role of the side chain gamma constituent in increasing the protein stability is consistent with this interpretation. Given these data, only representative single and double mutations involving positions 12 and 134 were deemed necessary to evaluate in the functional (i.e. 3T3 mitogenic) assay. All possible combinations of Cys, Val, and Thr single and double mutations at positions 12 and 134 comprise a total set of 15 mutations; however, based on the stability and structural data, we conclude that the single and double Val mutants characterized in the mitogenic assay are appropriately representative of the different combinations of Cys, Val and Thr mutations at these positions. The structure and stability data presented in this application allow us to predict the utility of the various Cys, Val and Thr mutations at positions 12 and 134.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES

1. Folkman, J., Angiogenesis: initiation and control. *Annals of the New York Academy of Science* 1982, 401, 212-227.
2. Thomas, K. A.; Rios-Candelore, M.; Gimenez-Gallego, G.; DiSalvo, J.; Bennett, C.; Rodkey, J.; Fitzpatrick, S., Pure brain-derived acidic fibroblast growth factor is a potent angiogenic vascular endothelial cell mitogen with sequence homology to interleukin 1. *Proceedings of the National Academy of Science USA* 1985, 82, (October), 6409-6413.
3. Stegmann, T. J.; Hoppert, T.; Schneider, A.; Popp, M.; Strupp, G.; Ibing, R. O.; Hertel, A., Therapeutic angiogenesis: intramyocardial growth factor delivery of FGF-1 as sole therapy in patients with chronic coronary artery disease. *Cardiac and Vascular Regeneration* 2000, 1, (4), 259-267.
4. McLachlan, A. D., Three-fold structural pattern in the soybean trypsin inhibitor (Kunitz). *Journal of Molecular Biology* 1979, 133, 557-563.
5. Murzin, A. G.; Lesk, A. M.; Chothia, C., β-trefoil fold. Patterns of structure and sequence in the kunitz inhibitors interleukins-1β and 1á and fibroblast growth factors. *Journal of Molecular Biology* 1992, 223, 531-543.
6. Bernett, M. J.; Somasundaram, T.; Blaber, M., An atomic resolution structure for human fibroblast growth factor 1. *Proteins* 2004, 57, 626-634.
7. Lozano, R. M.; Pineda-Lucena, A.; Gonzalez, C.; Angeles Jimenez, M.; Cuevas, P.; Redondo-Horcajo, M.; Sanz, J. M.; Rico, M.; Gimenez-Gallego, G., 1H NMR structural characterization of a nonmitogenic, vasodilatory, ischemia-protector and neuromodulatory acidic fibroblast growth factor. *Biochemistry* 2000, 39, (17), 4982-93.
8. Samuel, D.; Kumar, T. K. S.; Balamurugan, K.; Lin, W.-Y.; Chin, D.-H.; Yu, C., Structural events during the refolding of an all β-sheet protein. Journal of *Biological Chemistry* 2001, 276, 4134-4141.

9. Brych, S. R.; Dubey, V. K.; Bienkiewicz, E.; Lee, J.; Logan, T. M.; Blaber, M., Symmetric primary and tertiary structure mutations within a symmetric superfold: a solution, and not a constraint, to achieve a foldable polypeptide. *Journal of Molecular Biology* 2004, 344, 769-780.

10. Schreiber, G.; Buckle, A. M.; Fersht, A. R., Stability and function: two constraints in the evolution of barstar and other proteins. *Structure* 1994, 2, 945-951.

11. Shoichet, B. K.; Baase, W. A.; Kuroki, R.; Matthews, B. W., A relationship between protein stability and protein function. *Proc Natl Acad Sci USA* 1995, 92, (2), 452-6.

12. Wang, X.; Minasov, G.; Shoichet, B. K., Evolution of an antibiotic resistance enzyme constrained by stability and activity trade-offs. *Journal of Molecular Biology* 2002, 320, 85-95.

13. Bloom, J. D.; Wilke, C. O.; Arnold, F. H.; Adami, C., Stability and the evolvability of function in a model protein. *Biophysical Journal* 2004, 86, 2758-2764.

14. Jager, M.; Zhang, Y.; Bieschke, J.; Nguyen, H.; Dendle, M.; Bowman, M. E.; Noel, J. P.; Gruebele, M.; Kelly, J. W., Structure-function-folding relationship in a WW domain. *Proc Natl Acad Sci USA* 2006, 103, 10648-10653.

15. Blaber, S. I.; Culajay, J. F.; Khurana, A.; Blaber, M., Reversible thermal denaturation of human FGF-1 induced by low concentrations of guanidine hydrochloride. *Biophysical Journal* 1999, 77, (July), 470-477.

16. Culajay, J. F.; Blaber, S. I.; Khurana, A.; Blaber, M., Thermodynamic characterization of mutants of human fibroblast growth factor 1 with an increased physiological half-life. *Biochemistry* 2000, 39, (24), 7153-7158.

17. Brych, S. R.; Blaber, S. I.; Logan, T. M.; Blaber, M., Structure and stability effects of mutations designed to increase the primary sequence symmetry within the core region of a β-trefoil. *Protein Science* 2001, 10, 2587-2599.

18. Blaber, M.; DiSalvo, J.; Thomas, K. A., X-ray crystal structure of human acidic fibroblast growth factor. *Biochemistry* 1996, 35, 2086-2094.

19. Gimenez-Gallego, G.; Conn, G.; Hatcher, V. B.; Thomas, K. A., The complete amino acid sequence of human brain-derived acidic fibroblast growth factor. *Biochemical and Biophysical Research Communications* 1986, 128, (2), 611-617.

20. Linemeyer, D. L.; Menke, J. G.; Kelly, L. J.; Disalvo, J.; Soderman, D.; Schaeffer, M.-T.; Ortega, S.; Gimenez-Gallego, G.; Thomas, K. A., Disulfide bonds are neither required, present, nor compatible with full activity of human recombinant acidic fibroblast growth factor. *Growth Factors* 1990, 3, 287-298.

21. Ortega, S.; Schaeffer, M.-T.; Soderman, D.; DiSalvo, J.; Linemeyer, D. L.; GimenezGallego, G.; Thomas, K. A., Conversion of cysteine to serine residues alters the activity, stability, and heparin dependence of acidic fibroblast growth factor. *Journal of Biological Chemistry* 1991, 266, 5842-5846.

22. Dombkowski, A. A., Disulfide by Design: a computational method for the rational design of disulfide bonds in proteins. *Bioinformatics* 2003, 19, 1852-1853.

23. Brych, S. R.; Kim, J.; Logan, T. M.; Blaber, M., Accommodation of a highly symmetric core within a symmetric protein superfold. *Protein Science* 2003, 12, 2704-2718.

24. Eftink, M. R., The use of fluorescence methods to monitor unfolding transitions in proteins. *Biophysical Journal* 1994, 66, 482-501.

25. Pace, C. N.; Scholtz, J. M., Measuring the conformational stability of a protein. In *Protein structure: a practical approach*, Creighton, T. E., Ed. Oxford University Press: Oxford, 1997; pp 299-321.

26. Kim, J.; Brych, S. R.; Lee, J.; Logan, T. M.; Blaber, M., Identification of a key structural element for protein folding within β-hairpin turns. *Journal of Molecular Biology* 2003, (in press).

27. Fersht, A. R., *Kinetics of protein folding*. W.H. Freeman and Co.: New York, 1999.

28. Otwinowski, Z. In Oscillation data reduction program, *Proceedings of the CCP4 Study Weekend: "Data Collection and Processing"*, Jan. 29-30, 1993; Sawyer, L.; Isaacs, N.; Bailey, S., Eds. SERC Daresbury Laboratory, England: 1993; pp 56-62.

29. Otwinowski, Z.; Minor, W., Processing of x-ray diffraction data collected in oscillation mode. *Methods in Enzymology* 1997, 276, 307-326.

30. Brunger, A. T.; Adams, P. D.; Clore, G. M.; DeLano, W. L.; Gros, P.; Grosse-Kunstleve, R. W.; Jiang, J.-S.; Kuszewski, J.; Nilges, N.; Pannu, N. S.; Read, R. J.; Rice, L. M.; Simonson, T.; Warren, G. L., Crystallography and NMR system (CNS): A new software system for macromolecular structure determination. *Acta Crystallographica* 1998, D54, 905-921.

31. Jones, T. A.; Zou, J. Y.; Cowan, S. W.; Kjeldgaard, M., Improved methods for the building of protein models in electron density maps and the location of errors in these models. *Acta Crystallographica* 1991, A47, 110-119.

32. Brunger, A. T., Free R value: a novel statistical quantity for assessing the accuracy of crystal structures. *Nature* 1992, 355, (30 January), 472-475.

33. Connolly, M. L., The molecular surface package. *Journal of Molecular Graphics* 1993, 11, 139-141.

34. Bofill, R.; Searle, M. S., Engineering stabilizing β-sheet interactions into a conformationally flexible region in the folding transition state of ubiquitin. *Journal of Molecular Biology* 2005, 353, 373-384.

35. Copeland, R. A.; Ji, H.; Halfpenny, A. J.; Williams, R. W.; Thompson, K. C.; Herber, W. K.; Thomas, K. A.; Bruner, M. W.; Ryan, J. A.; Marquis-Omer, D.; Sanyal, G.; Sitrin, R. D.; Yamazaki, S.; Middaugh, C. R., The structure of human acidic fibroblast growth factor and its interaction with heparin. *Archives of Biochemistry and Biophysics* 1991, 289, (1), 53-61.

36. Thompson, J. A.; Haudenschild, C. C.; Anderson, K. D.; DiPietro, J. M.; Anderson, W. F.; Maciag, T., Heparin-binding growth factor 1 induces the formation of organoid neovascular structures in vivo. *Proceedings of the National Academy of Science USA* 1989, 86, (October), 7928-7932.

37. Plotnikov, A. N.; Schlessinger, J.; Hubbard, S. R.; Mohammadi, M., Structural basis for FGF receptor dimerization and activation. *Cell* 1999, 98, (5), 641-50.

That which is claimed:

1. A mutant polypeptide of human FGF1, said polypeptide comprising SEQ ID NO:1 wherein residue 12 is substituted by valine.

2. The mutant polypeptide of claim 1, further comprising residue 134 substituted by valine.

3. A mutant polypeptide of human FGF-1, said polypeptide comprising SEQ ID NO:1 wherein residue 134 is substituted by valine.

4. An isolated nucleic acid comprising a sequence that encodes a human FGF-1 polypeptide containing the amino acid sequence of SEQ ID NO:1 wherein residue 12 is substituted by valine.

5. The nucleic acid of claim 4, wherein the encoded FGF-1 polypeptide further comprises residue 134 substituted by valine.

6. An isolated nucleic acid comprising a sequence that encodes a human FGF-1 polypeptide containing the amino acid sequence of SEQ ID NO:1 wherein residue 134 is substituted by valine.

* * * * *